(12) United States Patent
Kladakis et al.

(10) Patent No.: US 8,551,135 B2
(45) Date of Patent: Oct. 8, 2013

(54) SCREW CATCH MECHANISM FOR PFO OCCLUDER AND METHOD OF USE

(75) Inventors: Stephanie M. Kladakis, Watertown, MA (US); Ryan Cahill, Brighton, MA (US)

(73) Assignee: W.L. Gore & Associates, Inc., Flagstaff, AZ (US)

( * ) Notice: Subject to any disclaimer, the term of this patent is extended or adjusted under 35 U.S.C. 154(b) by 0 days.

(21) Appl. No.: 11/729,045

(22) Filed: Mar. 28, 2007

(65) Prior Publication Data

US 2007/0276415 A1    Nov. 29, 2007

Related U.S. Application Data

(60) Provisional application No. 60/787,987, filed on Mar. 31, 2006.

(51) Int. Cl.
*A61B 17/08* (2006.01)
*A61B 17/122* (2006.01)
*A61B 17/00* (2006.01)

(52) U.S. Cl.
USPC .......................... 606/213; 606/139; 606/151

(58) Field of Classification Search
USPC ............... 606/213, 215, 151, 139, 200, 113, 606/191, 232, 108; 623/23.72; 128/831
See application file for complete search history.

(56) References Cited

U.S. PATENT DOCUMENTS

| | | |
|---|---|---|
| 3,824,631 A | 7/1974 | Burstein et al. |
| 3,874,388 A | 4/1975 | King et al. |
| 3,875,648 A | 4/1975 | Bone |
| 3,924,631 A | 12/1975 | Mancusi, Jr. |
| 4,006,747 A | 2/1977 | Kronenthal et al. |
| 4,007,743 A | 2/1977 | Blake |
| 4,149,327 A | 4/1979 | Hammer et al. |
| 4,425,908 A | 1/1984 | Simon |
| 4,610,674 A | 9/1986 | Suzuki et al. |

(Continued)

FOREIGN PATENT DOCUMENTS

| | | |
|---|---|---|
| DE | 9413645 U1 | 10/1994 |
| EP | 0362113 | 4/1990 |

(Continued)

OTHER PUBLICATIONS

Athanasion, T., "Coronary Artery Bypass with the Use of a Magnetic Distal Anastomotic Device: Surgical Technique and Preliminary Experience," The Heart Surgery Forum #2004-1024, 2004, 4 pgs.

(Continued)

*Primary Examiner* — Corrine M McDermott
*Assistant Examiner* — Mark Mashack
(74) *Attorney, Agent, or Firm* — DLA Piper LLP (US)

(57) ABSTRACT

Devices, delivery systems and delivery techniques for an occlusion device for the closure of physical anomalies, such as an atrial septal defect, a patent foramen ovale (PFO), and other septal and vascular defects are described. The devices, delivery systems and delivery techniques relate particularly to, but are not limited to, a patent foramen ovale (PFO) occluder made from a polymer tube, specifically, a petal-shaped occluder. In certain embodiments, the catch system includes a catch member with a screw catch mechanism for connecting to the occluder. A delivery system for use with the catch member includes a component for rotating the catch member relative to the occluder to engage the screw catch mechanism.

6 Claims, 9 Drawing Sheets

(56) References Cited

U.S. PATENT DOCUMENTS

| | | |
|---|---|---|
| 4,626,245 A | 12/1986 | Weinstein |
| 4,693,249 A | 9/1987 | Schenck et al. |
| 4,696,300 A | 9/1987 | Anderson |
| 4,710,181 A | 12/1987 | Fuqua |
| 4,710,192 A | 12/1987 | Liotta et al. |
| 4,738,666 A | 4/1988 | Fuqua |
| 4,836,204 A | 6/1989 | Landymore et al. |
| 4,840,623 A | 6/1989 | Quackenbush |
| 4,902,508 A | 2/1990 | Badylak et al. |
| 4,915,107 A | 4/1990 | Rebuffat et al. |
| 4,917,089 A | 4/1990 | Sideris |
| 4,921,479 A | 5/1990 | Grayzel |
| 4,956,178 A | 9/1990 | Badylak et al. |
| 5,021,059 A | 6/1991 | Kensey et al. |
| 5,037,433 A | 8/1991 | Wilk et al. |
| 5,041,129 A | 8/1991 | Hayhurst et al. |
| 5,049,131 A | 9/1991 | Deuss |
| 5,078,736 A | 1/1992 | Behl |
| 5,106,913 A | 4/1992 | Yamaguchi et al. |
| 5,108,420 A | 4/1992 | Marks |
| 5,149,327 A | 9/1992 | Oshiyama |
| 5,163,131 A | 11/1992 | Row et al. |
| 5,167,363 A | 12/1992 | Adkinson et al. |
| 5,167,637 A | 12/1992 | Okada et al. |
| 5,171,259 A | 12/1992 | Inoue |
| 5,176,659 A | 1/1993 | Mancini |
| 5,192,301 A | 3/1993 | Kamiya et al. |
| 5,222,974 A | 6/1993 | Kensey et al. |
| 5,226,879 A | 7/1993 | Ensminger et al. |
| 5,236,440 A | 8/1993 | Hlavacek |
| 5,245,023 A | 9/1993 | Peoples et al. |
| 5,245,080 A | 9/1993 | Aubard et al. |
| 5,250,430 A | 10/1993 | Peoples et al. |
| 5,257,637 A | 11/1993 | El Gazayerli |
| 5,275,826 A | 1/1994 | Badylak et al. |
| 5,282,827 A | 2/1994 | Kensey et al. |
| 5,284,488 A | 2/1994 | Sideris |
| 5,304,184 A | 4/1994 | Hathaway et al. |
| 5,312,341 A | 5/1994 | Turi |
| 5,312,435 A | 5/1994 | Nash et al. |
| 5,316,262 A | 5/1994 | Koebler |
| 5,320,611 A | 6/1994 | Bonutti et al. |
| 5,334,217 A * | 8/1994 | Das ................ 606/213 |
| 5,350,363 A | 9/1994 | Goode et al. |
| 5,354,308 A | 10/1994 | Simon et al. |
| 5,364,356 A | 11/1994 | Hofling |
| 5,411,481 A | 5/1995 | Allen et al. |
| 5,413,584 A | 5/1995 | Schulze |
| 5,417,699 A | 5/1995 | Klein et al. |
| 5,425,744 A | 6/1995 | Fagan et al. |
| 5,433,727 A | 7/1995 | Sideris |
| 5,451,235 A | 9/1995 | Lock et al. |
| 5,453,099 A | 9/1995 | Lee et al. |
| 5,478,353 A | 12/1995 | Yoon |
| 5,480,353 A | 1/1996 | Garza, Jr. |
| 5,480,424 A | 1/1996 | Cox |
| 5,486,193 A | 1/1996 | Bourne et al. |
| 5,507,811 A | 4/1996 | Koike et al. |
| 5,534,432 A | 7/1996 | Peoples et al. |
| 5,540,712 A | 7/1996 | Kleshinski et al. |
| 5,562,632 A | 10/1996 | Davila et al. |
| 5,577,299 A | 11/1996 | Thompson et al. |
| 5,601,571 A | 2/1997 | Moss |
| 5,603,703 A | 2/1997 | Elsberry et al. |
| 5,618,311 A | 4/1997 | Gryskiewicz |
| 5,620,461 A | 4/1997 | Muijs Van De Moer et al. |
| 5,626,599 A | 5/1997 | Bourne et al. |
| 5,634,936 A | 6/1997 | Linden et al. |
| 5,649,950 A | 7/1997 | Bourne et al. |
| 5,649,959 A | 7/1997 | Hannam et al. |
| 5,663,063 A | 9/1997 | Peoples et al. |
| 5,683,411 A | 11/1997 | Kavteladze et al. |
| 5,690,674 A | 11/1997 | Diaz |
| 5,693,085 A | 12/1997 | Buirge et al. |
| 5,702,421 A | 12/1997 | Schneidt |
| 5,709,707 A | 1/1998 | Lock et al. |
| 5,713,864 A | 2/1998 | Verkaart |
| 5,717,259 A | 2/1998 | Schexnayder |
| 5,720,754 A | 2/1998 | Middleman et al. |
| 5,725,552 A | 3/1998 | Kotula et al. |
| 5,733,294 A | 3/1998 | Forber et al. |
| 5,733,337 A | 3/1998 | Carr, Jr. et al. |
| 5,741,297 A | 4/1998 | Simon |
| 5,772,641 A | 6/1998 | Wilson |
| 5,776,162 A | 7/1998 | Kleshinski |
| 5,776,183 A | 7/1998 | Kanesaka et al. |
| 5,797,960 A | 8/1998 | Stevens et al. |
| 5,800,516 A | 9/1998 | Fine et al. |
| 5,810,884 A | 9/1998 | Kim |
| 5,820,594 A | 10/1998 | Fontirroche et al. |
| 5,823,956 A | 10/1998 | Roth et al. |
| 5,829,447 A | 11/1998 | Stevens et al. |
| 5,853,420 A | 12/1998 | Chevillon et al. |
| 5,853,422 A | 12/1998 | Huebsch et al. |
| 5,855,614 A | 1/1999 | Stevens et al. |
| 5,861,003 A | 1/1999 | Latson et al. |
| 5,865,791 A | 2/1999 | Whayne et al. |
| 5,879,366 A | 3/1999 | Shaw et al. |
| 5,893,856 A | 4/1999 | Jacob et al. |
| 5,895,411 A * | 4/1999 | Irie ................ 606/213 |
| 5,902,287 A | 5/1999 | Martin |
| 5,902,319 A | 5/1999 | Daley |
| 5,904,703 A | 5/1999 | Gilson |
| 5,919,200 A | 7/1999 | Stambaugh et al. |
| 5,924,424 A | 7/1999 | Stevens et al. |
| 5,928,250 A | 7/1999 | Koike et al. |
| 5,944,691 A | 8/1999 | Querns et al. |
| 5,944,738 A | 8/1999 | Amplatz et al. |
| 5,955,110 A | 9/1999 | Patel et al. |
| 5,976,174 A | 11/1999 | Ruiz |
| 5,980,505 A | 11/1999 | Wilson |
| 5,989,268 A | 11/1999 | Pugsley, Jr. et al. |
| 5,993,475 A | 11/1999 | Lin et al. |
| 5,993,844 A | 11/1999 | Abraham et al. |
| 5,997,575 A | 12/1999 | Whitson et al. |
| 6,010,517 A | 1/2000 | Baccaro |
| 6,019,753 A | 2/2000 | Pagan |
| 6,024,756 A | 2/2000 | Huebsch et al. |
| 6,027,519 A | 2/2000 | Stanford |
| 6,030,007 A | 2/2000 | Bassily et al. |
| 6,056,760 A | 5/2000 | Koike et al. |
| 6,071,998 A | 6/2000 | Muller et al. |
| 6,077,291 A | 6/2000 | Das |
| 6,077,880 A | 6/2000 | Castillo et al. |
| 6,079,414 A | 6/2000 | Roth |
| 6,080,182 A | 6/2000 | Shaw et al. |
| 6,096,347 A | 8/2000 | Geddes et al. |
| 6,106,913 A | 8/2000 | Scardino et al. |
| 6,113,609 A | 9/2000 | Adams |
| 6,117,159 A | 9/2000 | Huebsch et al. |
| 6,126,686 A | 10/2000 | Badylak et al. |
| 6,132,438 A | 10/2000 | Fleischman et al. |
| 6,143,037 A | 11/2000 | Goldstein et al. |
| 6,152,144 A | 11/2000 | Lesh et al. |
| 6,165,183 A | 12/2000 | Kuehn et al. |
| 6,165,204 A | 12/2000 | Levinson et al. |
| 6,168,588 B1 | 1/2001 | Wilson |
| 6,171,329 B1 | 1/2001 | Shaw et al. |
| 6,174,322 B1 | 1/2001 | Schneidt et al. |
| 6,174,330 B1 | 1/2001 | Stinson |
| 6,183,443 B1 | 2/2001 | Kratoska et al. |
| 6,187,039 B1 | 2/2001 | Hiles et al. |
| 6,190,353 B1 | 2/2001 | Makower et al. |
| 6,190,357 B1 | 2/2001 | Ferrari et al. |
| 6,197,016 B1 | 3/2001 | Fourkas et al. |
| 6,199,262 B1 | 3/2001 | Martin |
| 6,206,895 B1 | 3/2001 | Levinson |
| 6,206,907 B1 | 3/2001 | Marino et al. |
| 6,214,029 B1 | 4/2001 | Thill et al. |
| 6,217,590 B1 | 4/2001 | Levinson |
| 6,221,092 B1 | 4/2001 | Koike et al. |
| 6,227,139 B1 | 5/2001 | Nguyen et al. |
| 6,228,097 B1 | 5/2001 | Levinson et al. |
| 6,231,561 B1 | 5/2001 | Frazier et al. |

| | | | | | | |
|---|---|---|---|---|---|---|
| 6,245,080 B1 | 6/2001 | Levinson | | 7,918,872 B2 * | 4/2011 | Mitelberg et al. ............ 606/200 |
| 6,245,537 B1 | 6/2001 | Williams et al. | | 8,062,325 B2 * | 11/2011 | Mitelberg et al. ............ 606/200 |
| 6,261,309 B1 | 7/2001 | Urbanski | | 2001/0010481 A1 | 8/2001 | Blanc et al. |
| 6,265,333 B1 | 7/2001 | Dzenis et al. | | 2001/0014800 A1 | 8/2001 | Frazier et al. |
| 6,270,515 B1 * | 8/2001 | Linden et al. ............... 606/213 | | 2001/0025132 A1 | 9/2001 | Alferness et al. |
| 6,277,138 B1 | 8/2001 | Levinson et al. | | 2001/0034537 A1 | 10/2001 | Shaw et al. |
| 6,277,139 B1 | 8/2001 | Levinson et al. | | 2001/0034567 A1 | 10/2001 | Allen et al. |
| 6,287,317 B1 | 9/2001 | Makower et al. | | 2001/0037129 A1 | 11/2001 | Thill |
| 6,290,674 B1 | 9/2001 | Roue et al. | | 2001/0039435 A1 | 11/2001 | Roue et al. |
| 6,299,635 B1 | 10/2001 | Frantzen | | 2001/0039436 A1 | 11/2001 | Frazier et al. |
| 6,306,150 B1 | 10/2001 | Levinson | | 2001/0041914 A1 | 11/2001 | Frazier et al. |
| 6,306,424 B1 | 10/2001 | Vyakarnam et al. | | 2001/0041915 A1 | 11/2001 | Roue et al. |
| 6,312,443 B1 | 11/2001 | Stone | | 2001/0044639 A1 | 11/2001 | Levinson |
| 6,312,446 B1 | 11/2001 | Huebsch et al. | | 2001/0049492 A1 | 12/2001 | Frazier et al. |
| 6,315,791 B1 | 11/2001 | Gingras et al. | | 2002/0010481 A1 | 1/2002 | Jayaraman |
| 6,316,262 B1 | 11/2001 | Huisman et al. | | 2002/0019648 A1 | 2/2002 | Akerfeldt et al. |
| 6,319,263 B1 | 11/2001 | Levinson | | 2002/0022859 A1 | 2/2002 | Hogendijk |
| 6,322,548 B1 | 11/2001 | Payne et al. | | 2002/0022860 A1 | 2/2002 | Borillo et al. |
| 6,328,727 B1 | 12/2001 | Frazier et al. | | 2002/0026208 A1 | 2/2002 | Roe et al. |
| 6,334,872 B1 | 1/2002 | Termin et al. | | 2002/0029048 A1 | 3/2002 | Miller |
| 6,342,064 B1 | 1/2002 | Koike et al. | | 2002/0032459 A1 | 3/2002 | Horzewski et al. |
| 6,344,048 B1 | 2/2002 | Chin et al. | | 2002/0032462 A1 | 3/2002 | Houser et al. |
| 6,344,049 B1 | 2/2002 | Levinson et al. | | 2002/0034259 A1 | 3/2002 | Tada |
| 6,346,074 B1 | 2/2002 | Roth | | 2002/0035374 A1 | 3/2002 | Borillo et al. |
| 6,348,041 B1 | 2/2002 | Klint et al. | | 2002/0043307 A1 | 4/2002 | Ishida et al. |
| 6,352,552 B1 | 3/2002 | Levinson et al. | | 2002/0049457 A1 | 4/2002 | Kaplan et al. |
| 6,355,052 B1 | 3/2002 | Neuss et al. | | 2002/0052572 A1 | 5/2002 | Franco et al. |
| 6,356,782 B1 | 3/2002 | Sirimanne et al. | | 2002/0058989 A1 | 5/2002 | Chen et al. |
| 6,358,238 B1 | 3/2002 | Sherry | | 2002/0077555 A1 | 6/2002 | Schwartz |
| 6,364,853 B1 | 4/2002 | French et al. | | 2002/0095174 A1 | 7/2002 | Tsugita et al. |
| 6,371,904 B1 | 4/2002 | Sirimanne et al. | | 2002/0096183 A1 | 7/2002 | Stevens et al. |
| 6,375,625 B1 | 4/2002 | French et al. | | 2002/0099389 A1 | 7/2002 | Michler et al. |
| 6,375,671 B1 | 4/2002 | Kobayashi et al. | | 2002/0099390 A1 | 7/2002 | Kaplan et al. |
| 6,379,342 B1 | 4/2002 | Levinson | | 2002/0103492 A1 | 8/2002 | Kaplan et al. |
| 6,379,368 B1 | 4/2002 | Corcoran et al. | | 2002/0107531 A1 | 8/2002 | Schreck et al. |
| 6,387,104 B1 | 5/2002 | Pugsley, Jr. et al. | | 2002/0111537 A1 | 8/2002 | Taylor et al. |
| 6,398,796 B2 | 6/2002 | Levinson | | 2002/0111637 A1 | 8/2002 | Kaplan et al. |
| 6,402,772 B1 | 6/2002 | Amplatz et al. | | 2002/0111647 A1 | 8/2002 | Khairkhahan et al. |
| 6,419,669 B1 | 7/2002 | Frazier et al. | | 2002/0120323 A1 | 8/2002 | Thompson et al. |
| 6,426,145 B1 | 7/2002 | Moroni | | 2002/0128680 A1 | 9/2002 | Pavlovic |
| 6,436,088 B2 | 8/2002 | Frazier et al. | | 2002/0129819 A1 | 9/2002 | Feldman et al. |
| 6,440,152 B1 | 8/2002 | Gainor et al. | | 2002/0143292 A1 * | 10/2002 | Flinchbaugh ................. 604/107 |
| 6,450,987 B1 | 9/2002 | Kramer | | 2002/0164729 A1 | 11/2002 | Skraly et al. |
| 6,460,749 B1 | 10/2002 | Levinson et al. | | 2002/0169377 A1 | 11/2002 | Khairkhahan et al. |
| 6,478,773 B1 * | 11/2002 | Gandhi et al. ............... 604/113 | | 2002/0183786 A1 | 12/2002 | Girton |
| 6,482,224 B1 | 11/2002 | Michler et al. | | 2002/0183787 A1 | 12/2002 | Wahr et al. |
| 6,488,706 B1 | 12/2002 | Solymar et al. | | 2002/0183823 A1 | 12/2002 | Pappu |
| 6,494,846 B1 | 12/2002 | Margolis | | 2002/0198563 A1 | 12/2002 | Gainor et al. |
| 6,494,888 B1 | 12/2002 | Laufer et al. | | 2003/0004533 A1 | 1/2003 | Dieck et al. |
| 6,508,828 B1 | 1/2003 | Akerfeldt et al. | | 2003/0023266 A1 | 1/2003 | Welch et al. |
| 6,514,515 B1 | 2/2003 | Williams | | 2003/0028213 A1 | 2/2003 | Thill et al. |
| 6,548,569 B1 | 4/2003 | Williams et al. | | 2003/0045893 A1 | 3/2003 | Ginn |
| 6,551,303 B1 | 4/2003 | Van Tassel et al. | | 2003/0050665 A1 | 3/2003 | Ginn |
| 6,551,344 B2 | 4/2003 | Thill | | 2003/0055455 A1 * | 3/2003 | Yang et al. ................... 606/215 |
| 6,585,719 B2 | 7/2003 | Wang | | 2003/0057156 A1 | 3/2003 | Peterson et al. |
| 6,585,755 B2 | 7/2003 | Jackson et al. | | 2003/0059640 A1 | 3/2003 | Marton et al. |
| 6,596,013 B2 | 7/2003 | Yang et al. | | 2003/0065379 A1 | 4/2003 | Babbs et al. |
| 6,599,448 B1 | 7/2003 | Ehrhard, Jr. et al. | | 2003/0100920 A1 | 5/2003 | Akin et al. |
| 6,610,764 B1 | 8/2003 | Martin et al. | | 2003/0120337 A1 | 6/2003 | Van Tassel et al. |
| 6,623,508 B2 | 9/2003 | Shaw et al. | | 2003/0139819 A1 * | 7/2003 | Beer et al. .................. 623/23.71 |
| 6,623,518 B2 | 9/2003 | Thompson et al. | | 2003/0171774 A1 | 9/2003 | Freudenthal et al. |
| 6,626,936 B2 | 9/2003 | Stinson | | 2003/0191495 A1 | 10/2003 | Ryan et al. |
| 6,629,901 B2 | 10/2003 | Huang | | 2003/0195530 A1 | 10/2003 | Thill |
| 6,666,861 B1 | 12/2003 | Grabek | | 2003/0204203 A1 | 10/2003 | Khairkhahan et al. |
| 6,669,713 B2 * | 12/2003 | Adams ........................... 606/213 | | 2004/0044361 A1 | 3/2004 | Frazier et al. |
| 6,669,722 B2 | 12/2003 | Chen et al. | | 2004/0073242 A1 | 4/2004 | Chanduszko |
| 6,689,589 B2 | 2/2004 | Huisman et al. | | 2004/0133236 A1 | 7/2004 | Chanduszko |
| 6,712,804 B2 | 3/2004 | Roue et al. | | 2004/0176799 A1 | 9/2004 | Chanduszko et al. |
| 6,712,836 B1 | 3/2004 | Berg et al. | | 2004/0210301 A1 | 10/2004 | Obermiller |
| 6,726,696 B1 | 4/2004 | Houser et al. | | 2004/0234567 A1 | 11/2004 | Dawson |
| 6,828,357 B1 | 12/2004 | Martin et al. | | 2005/0025809 A1 | 2/2005 | Hasirci et al. |
| 6,838,493 B2 | 1/2005 | Williams et al. | | 2005/0043759 A1 * | 2/2005 | Chanduszko ................. 606/213 |
| 6,855,126 B2 * | 2/2005 | Flinchbaugh ................. 604/106 | | 2005/0113868 A1 | 5/2005 | Devellian et al. |
| 6,867,247 B2 | 3/2005 | Williams et al. | | 2005/0182426 A1 * | 8/2005 | Adams et al. ................. 606/142 |
| 6,867,248 B1 | 3/2005 | Martin et al. | | 2005/0267523 A1 | 12/2005 | Devellian et al. |
| 6,867,249 B2 | 3/2005 | Lee et al. | | 2005/0273135 A1 * | 12/2005 | Chanduszko et al. ........ 606/213 |
| 6,921,410 B2 | 7/2005 | Porter | | 2005/0288706 A1 * | 12/2005 | Widomski et al. ........... 606/213 |
| 7,223,271 B2 * | 5/2007 | Muramatsu et al. .......... 606/143 | | 2005/0288786 A1 | 12/2005 | Chanduszko |
| 7,871,419 B2 * | 1/2011 | Devellian et al. ............ 606/157 | | 2006/0122647 A1 | 6/2006 | Callaghan et al. |

| | | | |
|---|---|---|---|
| 2006/0265004 A1 | 11/2006 | Callaghan et al. | |
| 2006/0271089 A1 | 11/2006 | Alejandro et al. | |
| 2007/0010851 A1 | 1/2007 | Chanduszko et al. | |
| 2007/0167981 A1 | 7/2007 | Opolski | |

FOREIGN PATENT DOCUMENTS

| | | |
|---|---|---|
| EP | 0474887 A1 | 3/1992 |
| EP | 0 839 549 | 5/1998 |
| EP | 0 861 632 | 9/1998 |
| EP | 1013227 A2 | 6/2000 |
| EP | 1046375 A1 | 10/2000 |
| EP | 1222897 A2 | 7/2002 |
| WO | WO-96/25179 A1 | 8/1996 |
| WO | WO-96/31157 | 10/1996 |
| WO | WO-98/07375 A1 | 2/1998 |
| WO | WO-98/08462 | 3/1998 |
| WO | WO-98/16174 | 4/1998 |
| WO | WO-98/29026 | 7/1998 |
| WO | WO-98/51812 | 11/1998 |
| WO | WO-99/05977 | 2/1999 |
| WO | WO-98/18864 | 4/1999 |
| WO | WO-99/18862 | 4/1999 |
| WO | WO-99/18864 | 4/1999 |
| WO | WO-99/18870 | 4/1999 |
| WO | WO-99/18871 | 4/1999 |
| WO | WO-99/30640 | 6/1999 |
| WO | WO-99/66846 | 12/1999 |
| WO | WO-00/27292 A1 | 5/2000 |
| WO | WO-00/44428 A2 | 8/2000 |
| WO | WO-01/08600 | 2/2001 |
| WO | WO-01/19256 | 3/2001 |
| WO | WO-01/21247 | 3/2001 |
| WO | WO-01/28432 | 4/2001 |
| WO | WO-01/30268 | 5/2001 |
| WO | WO-01/78596 | 10/2001 |
| WO | WO-01/93783 | 12/2001 |
| WO | WO-02/17809 | 3/2002 |
| WO | WO-02/24106 | 3/2002 |
| WO | WO-03/001893 | 1/2003 |
| WO | WO-03/024337 | 3/2003 |
| WO | WO-03/053493 A2 | 7/2003 |
| WO | WO-03/059152 | 7/2003 |
| WO | WO-03/063732 A | 8/2003 |
| WO | WO-03/077733 | 9/2003 |
| WO | WO-03/082076 | 10/2003 |
| WO | WO-03/103476 | 12/2003 |
| WO | WO-2004/032993 | 4/2004 |
| WO | WO-2004/037333 | 5/2004 |
| WO | WO-2004/043266 | 5/2004 |
| WO | WO-2004/043508 | 5/2004 |
| WO | WO-2004/052213 | 6/2004 |
| WO | WO-2005/006990 | 1/2005 |
| WO | WO-2005/018728 | 3/2005 |
| WO | WO-2005/027752 | 3/2005 |
| WO | WO-2005/074813 | 8/2005 |
| WO | WO-2005/092203 | 10/2005 |
| WO | WO-2005/110240 | 11/2005 |
| WO | WO-2005/112779 | 12/2005 |
| WO | WO-2006/036837 | 4/2006 |
| WO | WO-2006/102213 | 9/2006 |

OTHER PUBLICATIONS

Bachthaler, M. et al., "Corrosion of Tungsten Coils After Peripheral Vascular Embolization Theraphy: Influence on Outcome and Tungsten Load", *Catherization and Cardiovascular Interventions*, vol. 62, pp. 380-384, 2004.
European Examination Report, European Application No. 04781644.2, mailed Aug. 23, 2007 (3 Pages).
Falk, V., "Facilitated Endoscopic Beating Heart Coronary Artery Bypass Grafting Using a Magentic Coupling Device," Journal of Thoracic and Cardiovascular Surgery, vol. 126,(5), pp. 1575-1579.
Filsoufi, F., et al., "Automated Distal Coronary Bypass with a Novel Magnetic Coupler (MVP system)," J. Thoracic and Cardiovascular Surgery, vol. 127(1), pp. 185-192.
International Search Report, International Application No. PCT/US02/40850 mailed Jun. 19, 2003 (4 pgs).
International Search Report, International Application No. PCT/US03/01050, mailed Jul. 8, 2003 (1 pg).
International Search Report, International Application No. PCT/US03/09051, mailed Sep. 29, 2003 (2 pgs).
International Search Report, International Application No. PCT/US03/17390, mailed Oct. 6, 2003 (2 pgs).
International Search Report, International Application No. PCT/US03/17715, mailed Mar. 24, 2004 (2 pgs).
International Search Report, International Application No. PCT/US03/32133, mailed Apr. 22, 2004 (1 pg).
International Search Report, International Application No. PCT/US03/34003 mailed Oct. 3, 2004 (4 pgs).
International Search Report, International Application No. PCT/US03/35479, mailed Apr. 14, 2004 (2 pgs).
International Search Report, International Application No. PCT/US03/35998 mailed Jun. 16, 2004 (5 pgs).
International Search Report, International Application No. PCT/US03/39253, mailed Apr. 19, 2004 (4 pgs).
International Search Report, International Application No. PCT/US04/022643, mailed Mar. 31, 2005 (2 pgs).
International Search Report, International Application No. PCT/US04/026998, mailed Apr. 22, 2005 (5 pgs).
International Search Report, International Application No. PCT/US04/029978, mailed Jan. 26, 2005 (3 pgs).
International Search Report, International Application No. PCT/US05/006703, mailed Jul. 25, 2005 (3 pgs).
International Search Report, International Application No. PCT/US05/013705 mailed Aug. 4, 2005 (4 pgs).
International Search Report, International Application No. PCT/US05/015382, mailed Oct. 6, 2005 (4 pgs).
International Search Report, International Application No. PCT/US06/009978, mailed Jul. 13, 2006 (2 pgs).
International Search Report, International Application No. PCT/US07/065532, mailed Sep. 14, 2007 (5 pgs).
International Search Report, International Application No. PCT/US2007/065526, mailed Aug. 8, 2007 (4 pgs).
International Search Report, International Application No. PCT/US2007/065541, mailed Aug. 7, 2007 (4 pgs).
International Search Report, International Application No. PCT/US97/14822, mailed Feb. 20, 1998 (2 pgs).
International Search Report, International Application No. PCT/US97/17927, mailed Feb. 10, 1998 (1 pg).
Isotalo, T. et al., "Biocompatibility Testing of a New Bioabsorbable X-Ray Positive SR-PLA 96/4 Urethral Stent", *The Journal of Urology*, vol. 163, pp. 1764-1767, Nov. 1999.
Kimura, A., et al., "Effects of Neutron Irradiation on the Transformation Behavior in Ti—Ni Alloys," Abstract, Proceedings of the Int'l Conf. on Mariensitic Transformations, 1992, pp. 935-940.
Klima, U., "Magnetic Vascular Port in Minimally Invasive Direct Coronary Artery Bypass Grafting," Circulation, 2004, II-55-II-60.
Meier, MD, Bernhard et al., "Contemporary Management of Patent Foramen Ovale," American Heart Association, Inc., Circulation, 2003, vol. 107, pp. 5-9.
Nat'l Aeronautics and Space Administration, "55-Nitinol—The Alloy with a Memory: Its Physical Metallurgy, Properties and Applications," NASA Report, pp. 24-25.
Parviainen, M. et al., "A New Biodegradable Stent for the Pancreaticojejunal Anastomosis After Pancreaticoduodenal Resection: In Vitro Examination and Pilot Experiences in Humans", *Pancreas*, vol. 21, No. 1, pp. 14-21, 2000.
Ramanathan, G., et al., "Experimental and Computational Methods for Shape Memory Alloys," 15th ASCE Engineering Mechanics Conference, Jun. 2-5, 2002.
Ruddy, A.C. et al., "Rheological, Mechanical and Thermal Behaviour of Radipaque Filled Polymers", *Polymer Processing Research Centre, School of Chemical Engineering, Queen's University of Belfast* , 5 pages.
Ruiz, et al., "The Puncture Technique: a New Method for Transcatheter Closure of Patent Foramen Ovale," Catheterization and Cardiovascular Interventions, 2001, vol. 53, pp. 369-372.
Shabalovskaya, S., "Surface, Corrosion amd Biocompatibility Aspects of Nitinol as and Implant Material," Bio-Medical Materials and Engineering, 2002, vol. 12, pp. 69-109.

SMST-2000, "Proceedings of the International Conference on Shape Memory and Superelastic Technologies," Apr. 30 to May 4, 2000, Asilomar Conference Center (3 pgs).

Stockel, "Nitinol Medical Devices and Implants," SMST-2000 Conference Proceedings, 2001, pp. 531-541.

Uchil, J., "Shape Memory Alloys—Characterization Techniques," Pramana—Journal of Physics, 2002, vol. 58(5)(6), pp. 1131-1139.

Vaajanen, A. et al., "Expansion and Fixation Properties of a New Braided Biodegradable Urethral Stent: an Experimental Study in the Rabbit", *The Journal of Urology*, vol. 169, pp. 1771-1174, Mar. 2003.

European Examination Report, European Application No. 03729663.9, mailed Jul. 16, 2008 (5 Pages).

European Examination Report, European Application No. 03731562.9, mailed Jul. 18, 2008 (3 Pages).

European Examination Report, European Application No. 03779297.5, mailed Mar. 15, 2007 (6 Pages).

European Search Report, European Application No. 03729663.9, mailed Feb. 20, 2008 (3 Pages).

International Search Report and Written Opinion, International Patent Application No. PCT/US06/41255, mailed Jun. 13, 2008 (6 pgs).

International Search Report and Written Opinion, International Patent Application No. PCT/US08/59429, mailed Sep. 5, 2008 (9 pgs).

International Search Report for International Patent Application No. PCT/AU03/00759, filed Jun. 19, 2003.

International Search Report, International Application No. PCT/US05/34276, mailed Oct. 9, 2007.

International Search Report, International Patent Application No. PCT/US07/065546, mailed Oct. 29, 2007. 4 pages.

* cited by examiner

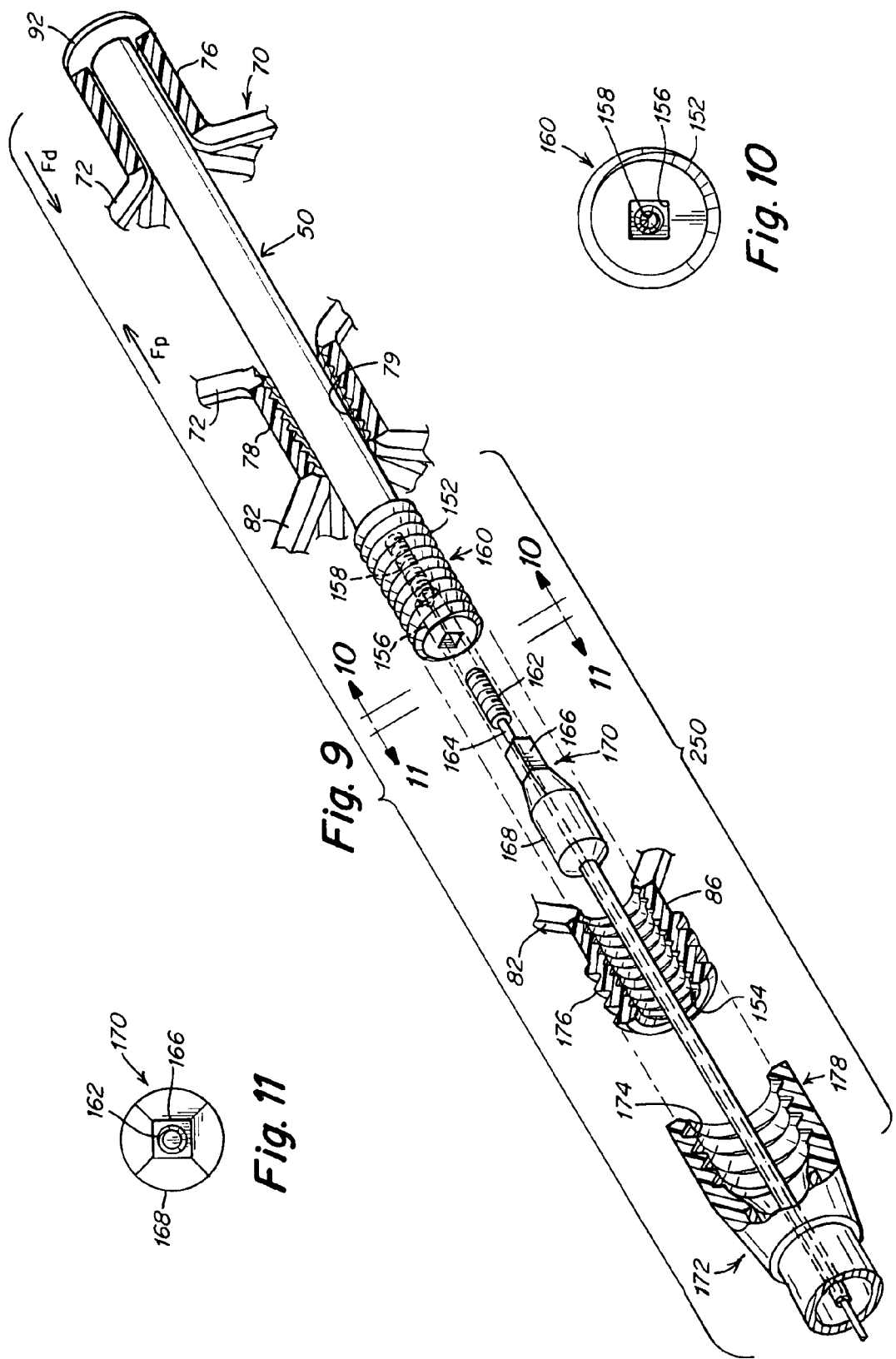

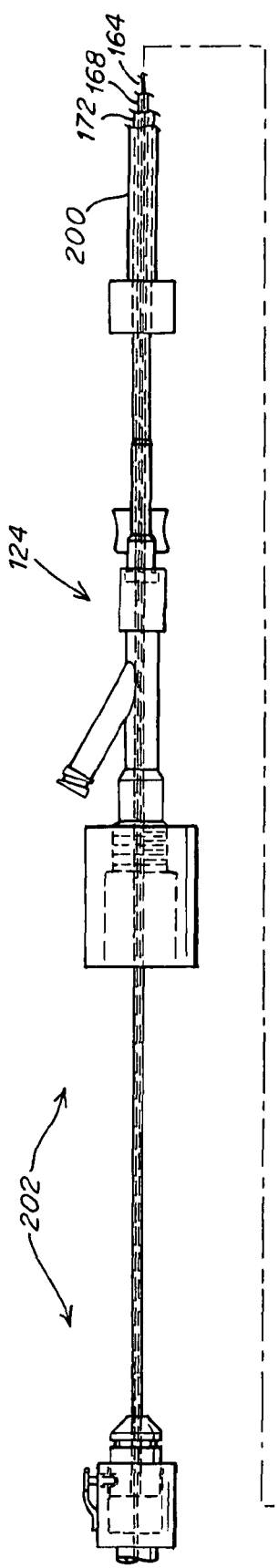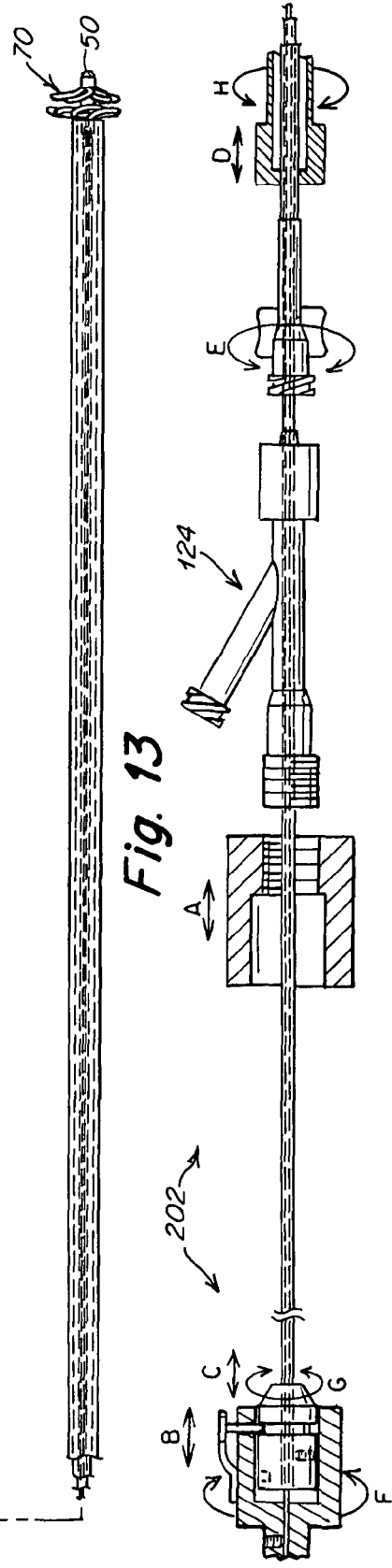
Fig. 13
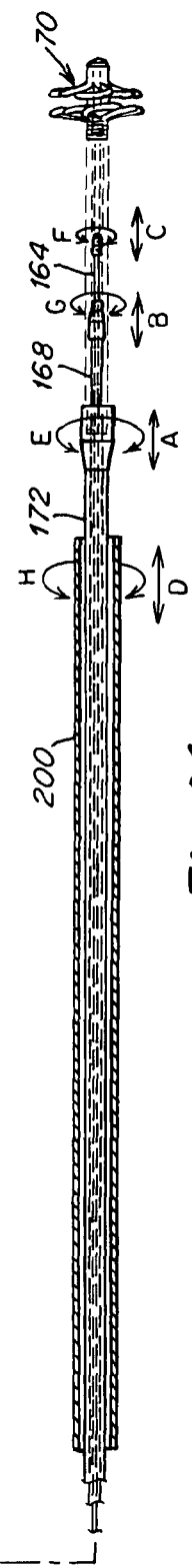
Fig. 14

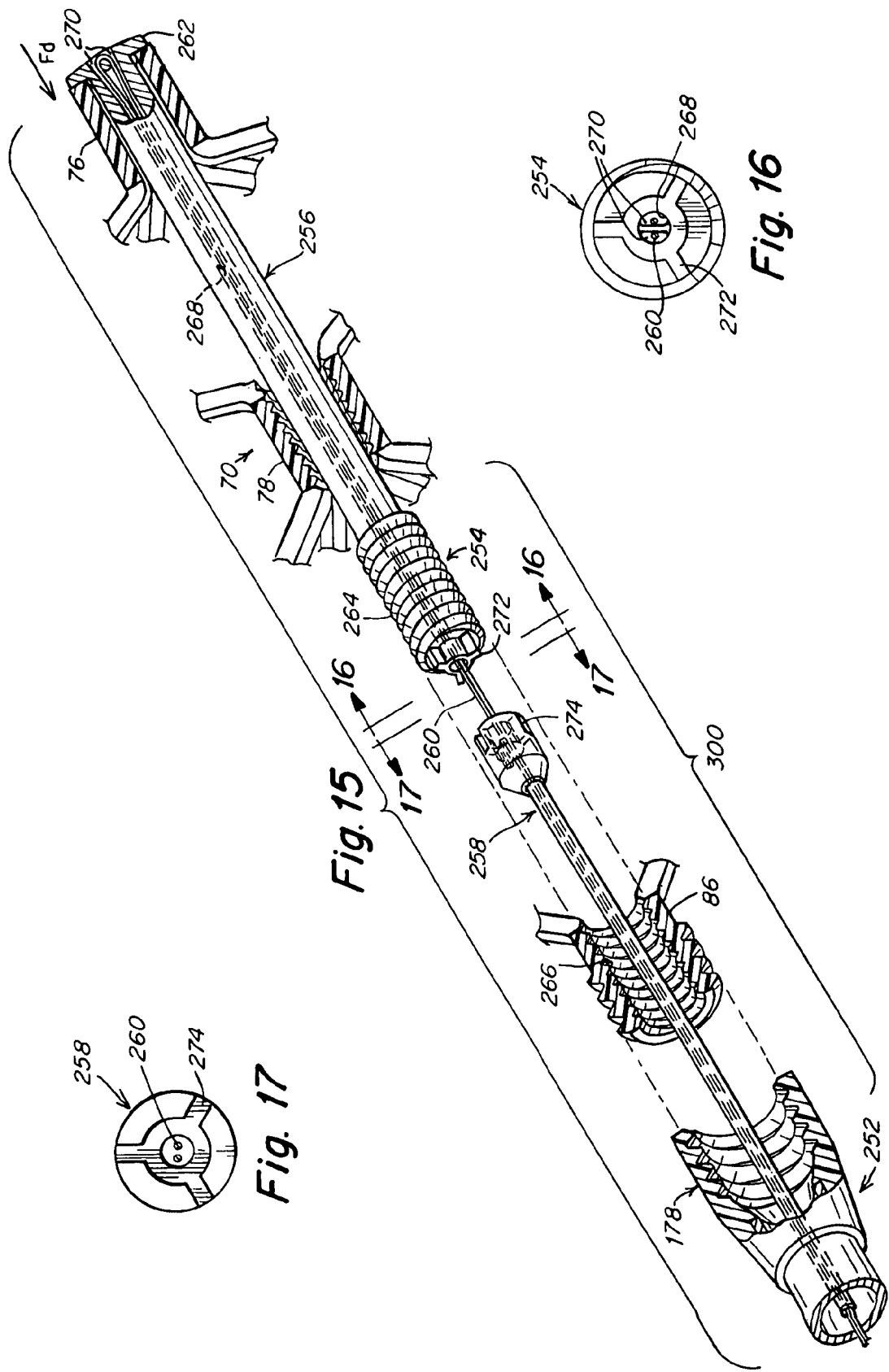

SCREW CATCH MECHANISM FOR PFO OCCLUDER AND METHOD OF USE

CROSS-REFERENCE TO RELATED APPLICATIONS

This Application claims the benefit under 35 U.S.C. 119(e) of U.S. Provisional Application No. 60/787,987, filed on Mar. 31, 2006, which is incorporated by reference herein in its entirety.

FIELD OF THE INVENTION

This invention relates generally to occlusion devices for the closure of physical anomalies, such as an atrial septal defect, a patent foramen ovale, and other septal and vascular defects. In particular, this invention relates to a catch mechanism to maintain the occluder in the deployed configuration. The invention also relates to delivery systems and mechanisms for such devices.

BACKGROUND OF THE INVENTION

A patent foramen ovale (PFO), illustrated in FIG. 1, is a persistent, one-way, usually flap-like opening in the wall between the right atrium 11 and left atrium 13 of the heart 10. Because left atrial (LA) pressure is normally higher than right atrial (RA) pressure, the flap usually stays closed. Under certain conditions, however, right atrial pressure can exceed left atrial pressure, creating the possibility that blood could pass from the right atrium 11 to the left atrium 13 and blood clots could enter the systemic circulation. It is desirable that this circumstance be eliminated.

The foramen ovale serves a desired purpose when a fetus is gestating. Because blood is oxygenated through the umbilical cord, and not through the developing lungs, the circulatory system of the fetal heart allows the blood to flow through the foramen ovale as a physiologic conduit for right-to-left shunting. After birth, with the establishment of pulmonary circulation, the increased left atrial blood flow and pressure results in functional closure of the foramen ovale. This functional closure is subsequently followed by anatomical closure of the two overlapping layers of tissue: septum primum 14 and septum secundum 16. However, a PFO has been shown to persist in a number of adults.

The presence of a PFO is generally considered to have no therapeutic consequence in otherwise healthy adults. Paradoxical embolism via a PFO is considered in the diagnosis for patients who have suffered a stroke or transient ischemic attack (TIA) in the presence of a PFO and without another identified cause of ischemic stroke. While there is currently no definitive proof of a cause-effect relationship, many studies have confirmed a strong association between the presence of a PFO and the risk for paradoxical embolism or stroke. In addition, there is significant evidence that patients with a PFO who have had a cerebral vascular event are at increased risk for future, recurrent cerebrovascular events. The presence of a PFO has also been linked to another condition, chronic migraine headaches. While researchers are still working on finding an explanation, PFO closure has been shown to eliminate or significantly reduce migraine headaches in many patients.

In certain cases, such as when anticoagulation is contraindicated, surgery may be necessary or desirable to close a PFO. The surgery would typically include suturing a PFO closed by attaching septum secundum to septum primum. This sutured attachment can be accomplished using either an interrupted or a continuous stitch and is a common way a surgeon shuts a PFO under direct visualization.

Umbrella devices and a variety of other similar mechanical closure devices, developed initially for percutaneous closure of atrial septal defects (ASDs), have been used in some instances to close PFOs. These devices potentially allow patients to avoid the side effects often associated with anticoagulation therapies and the risks of invasive surgery. However, umbrella devices and the like that are designed for ASDs are not optimally suited for use as PFO closure devices.

Currently available septal closure devices present drawbacks, including technically complex implantation procedures. Additionally, there are significant complications due to thrombus, fractures of the components, conduction system disturbances, perforations of heart tissue, and residual leaks. Many devices have a high septal profile and include large masses of foreign material, which may lead to unfavorable body adaptation of a device. Given that ASD devices are designed to occlude holes, many lack anatomic conformability to the flap-like anatomy of PFOs. Thus, when inserting an ASD device to close a PFO, the narrow opening and the thin flap may form impediments to proper deployment. Even if an occlusive seal is formed, the device may be deployed in the heart on an angle, leaving some components insecurely seated against the septum and, thereby, risking thrombus formation due to hemodynamic disturbances. Finally, some septal closure devices are complex to manufacture, which may result in inconsistent product performance.

Various devices and delivery systems have been developed to deliver occluders and other medical devices through body lumens. Some delivery systems of the prior art are used to deliver devices that readily expand to a delivered configuration when removed from the delivery system. Other occluders do not readily expand into a deployed configuration and techniques are used to change the configuration of the device into the deployed configuration. In the latter case, once an occluder is delivered to the desired delivery site and deployed, the occluder must have a catch system that keeps the device in the deployed configuration.

The devices and techniques disclosed herein are designed to address these and other deficiencies of prior art septal closure devices and techniques for delivering and retrieving such devices.

SUMMARY OF THE INVENTION

This description discloses a delivery system and technique(s) for delivering an implant into a desired location within the body and securing the device in the deployed configuration. The device(s) relate particularly to, but are not limited to, a septal occluder made from a polymer tube. The occluder includes a first side adapted to be disposed on one side of the septal tissue and a second side adapted to be disposed on the opposite side of the septal tissue. The first and second sides are adapted to occlude the aperture upon deployment of the device at its intended delivery location. The delivery technique, in addition to use with septal occluders, could be applied to other medical devices, such as other expandable devices constructed from an underlying tubular structure.

In one embodiment, the present invention provides a catch system that maintains the configuration of an occluder once it has been deployed. In one aspect, the catch system includes a catch member having a threaded outside surface at the proximal end that can be threadably attached to the proximal side of the occluder. The distal end of the catch member includes a flange that can apply a proximal force on the distal end of the occluder. A delivery wire having a threaded outside surface at the distal end can be threadably attached to the proximal or distal end of the catch member, so that by pulling the delivery wire in the proximal direction, a proximal force is applied to the catch member and the distal end of the occluder. The delivery system also includes a delivery catheter that can be threadably attached to the proximal end of the occluder and can be used to maintain the position thereof. During deployment, the delivery wire can be used to pull the distal end of the occluder in the proximal direction, thereby converting the occluder into an expanded profile, deployed configuration. An inner catheter having a key that fits inside a slot at the proximal end of the catch member is provided to apply an axial twisting force upon the catch member. Using the inner catheter, the proximal ends of the catch member and the occluder can be threadably attached or detached.

Before deployment, various components of the delivery system, catch system and the occluder in a reduced profile configuration can be connected and placed inside a delivery sheath. After moving the distal end of the delivery sheath past an aperture in the septum, the delivery sheath can be retracted. The delivery wire can then be used to convert the occluder to the expanded profile deployed configuration to occlude the aperture. The inner catheter can then be used to attach the proximal ends of the catch member and the occluder so that the occluder maintains the deployed configuration. After attachment, the delivery catheter can be detached from the occluder and removed. The occluder can later be retrieved if desired.

In another aspect, the catch system includes a catch member having a threaded outside surface at the proximal end that can be threadably attached to the proximal side of the occluder. The distal end of the catch member includes a flange that can apply a proximal force on the distal end of the occluder. A delivery wire forms a loop around the distal end of the catch member. Two apertures may be used to loop the delivery wire around the distal end. The delivery wire could be a polymeric material or metallic material. In some embodiments it could be Nitinol. In some embodiments, a delivery wire that can translate axial force in a pushing direction may be advantageous. The delivery system also includes a delivery catheter that can be threadably attached to the proximal end of the occluder and can be used to maintain the position thereof. During deployment, the delivery wire can be used to pull the distal end of the occluder in the proximal direction, thereby converting the occluder into an expanded profile, deployed configuration. An inner catheter having a slot at the distal end that fits a key at the proximal end of the catch member is provided to apply an axial twisting force upon the catch member. Using the inner catheter, the proximal ends of the catch member and the occluder can be threadably attached or detached.

According to at least some embodiments, the occluder is formed from a tube. According to some embodiments, the tube includes a material selected from the group consisting of metals, shape memory materials, alloys, polymers, bioabsorbable polymers, and combinations thereof. In particular embodiments, the tube includes a shape memory polymer. In particular embodiments, the tube includes nitinol. In some embodiments, the tube is formed by rolling a flat piece of material into a tubular form. According to some embodiments, the occluder is formed by cutting the tube. In other embodiments, the occluder is formed from a plurality of filaments, aligned in a tubular arrangement and bonded at selected locations. The occluder is placed in its deployment configuration by reducing the axial length of the device.

These and other aspects and embodiments of the invention are illustrated and described below.

BRIEF DESCRIPTION OF THE DRAWINGS

FIG. 9 is an exploded view of components of a delivery system for an occluder in accordance with an embodiment of the present invention;

FIGS. 10 and 11 are end views of the catch member and inner catheter of FIG. 9 respectively, as seen along lines 10-10 and 11-11.

FIGS. 13 and 14 are partial cross-sectional views of a delivery system for an occluder of the present invention;

FIG. 15 is an exploded view of components of a delivery system and occluder in accordance with another embodiment of the present invention;

FIGS. 16 and 17 are end views of the catch member and inner catheter of FIG. 15 respectively, as seen along lines 16-15 and 17-17.

DETAILED DESCRIPTION OF THE ILLUSTRATED EMBODIMENTS

In various aspects, the present invention provides devices, delivery/retrieval systems and techniques for delivering such devices intended to occlude an aperture within body tissue. In particular and as described in detail below, the described occluder may be used for closing an ASD, ventricular septal defect (VSD) or PFO in the atrial septum of a heart. Although the embodiments are described with reference to an ASD, VSD or PFO, one skilled in the art will recognize that the device and methods of the present invention may be used to treat other anatomical conditions. As such, the invention should not be considered limited in applicability to any particular anatomical condition. In addition, the systems and methods for delivery and retrieval, and for catching a device in a deployed state, that are aspects of the present invention may also be used in connection with other types of devices besides an occluder, in particular, devices having tubular profiles.

Figure 1:
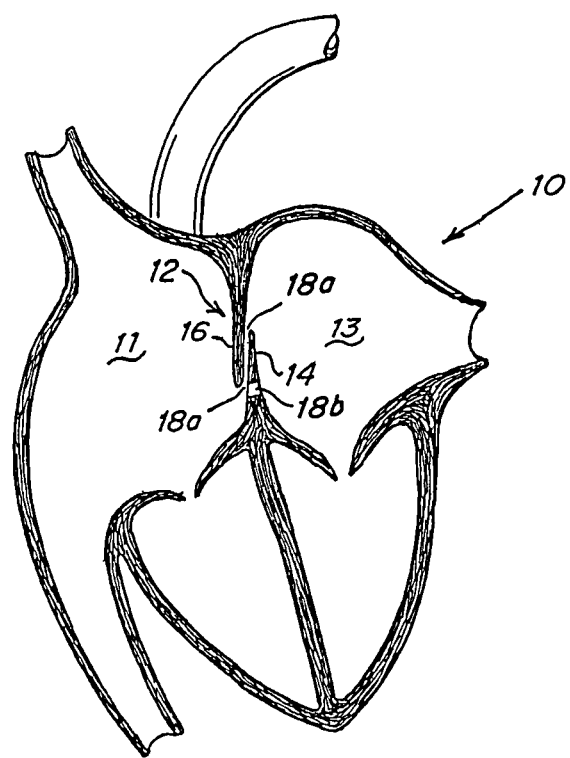
FIG. 1 is a schematic representation of a human heart including various septal defects.

FIG. 1 illustrates a human heart 10, having a right atrium 11 and a left atrium 13 and including various anatomical apertures 18a and 18b. The atrial septum 12 includes septum primum 14 and septum secundum 16. The anatomy of the septum 12 varies widely within the population. In some people, septum primum 14 extends to and overlaps with septum secundum 16. The septum primum 14 may be quite thin. When the anatomical apertures 18a is present, blood could travel through the anatomical aperture 18a between septum primum 14 and septum secundum 16 (referred to as "the PFO tunnel"). Additionally or alternatively, blood could travel through the anatomical aperture 18b (referred to as ASD).

In this application, "distal" refers to the direction away from a catheter insertion location and "proximal" refers to the direction nearer the insertion location. Additionally, the term "delivery configuration" refers to the configuration of a device, such as an occluder, when it has a reduced profile in a delivery catheter. The term "deployed configuration" refers to the configuration of the device, such as an occluder, when it has an expanded profile, such as deployed from the catheter at the desired implantation location.

Figure 2:
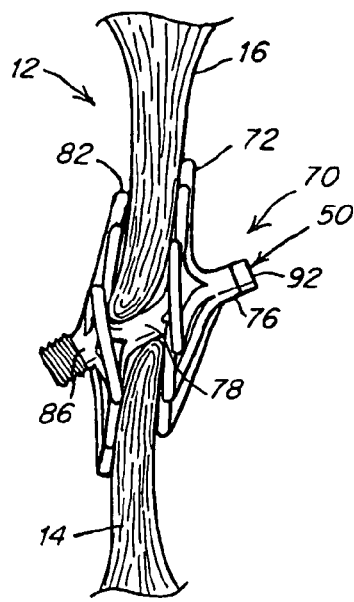
FIG. 2 illustrates a deployed occluder according to an aspect of the invention.

FIG. 2 illustrates an exemplary occluder with which systems and techniques disclosed herein may be used. An occluder 70, for example, is illustrated as deployed in the septum 12 of a heart. The occluder 70 operates to close an aperture in the septum by covering the sides of the aperture. The reference numerals used to identify components of the described embodiment are disposed on multiple figures where the component is illustrated. The reference numerals are intended to facilitate an overall understanding of the invention and the relationship between components illustrated in different figures.

The embodiment described in conjunction with FIGS. 5-8 has some similarities to the device disclosed in or can be used in conjunction with catch mechanisms and delivery/retrieval systems and techniques disclosed in U.S. patent application Ser. No. 10/890,784, entitled Tubular Patent Foramen Ovale (PFO) Closure Device with Catch System filed on Jul. 14, 2004; U.S. patent application Ser. No. 11/395,718, entitled Tubular Patent Foramen Ovale (PFO) Closure Device with Catch System, filed Mar. 31, 2006; U.S. patent application Ser. No. 11/384,635, filed Mar. 20, 2006, entitled Catch Member for PFO Occluder; U.S. patent application Ser. No. 11/235,661, filed Sep. 26, 2005, entitled Occluder Device Double Securement System for Delivery/Recovery of Such Occluder Device; U.S. patent application Ser. No. 11/121,833, entitled Catching Mechanisms for Tubular Septal Occluder, filed May 4, 2005; U.S. Pat. App. Ser. No. 60/787,988, entitled Deformable Flap Catch Mechanism for Occluder Device, filed Mar. 31, 2006; U.S. patent application Ser. No. 11/644,373, entitled Catch Members for Occluder Devices, filed Dec. 21, 2006; and U.S. patent application Ser. No. 11/728,694, entitled Patent Foramen Ovale (PFO) closure Device with Linearly Elongating Petals, filed Mar. 27, 2007, all of which have the same assignee as the present application, and are incorporated herein by reference in their entirety. These incorporated documents describe some ways in which a device can be formed by making cuts or slits in a tube and compressing the ends, and how to deliver such a device.

Figure 5:
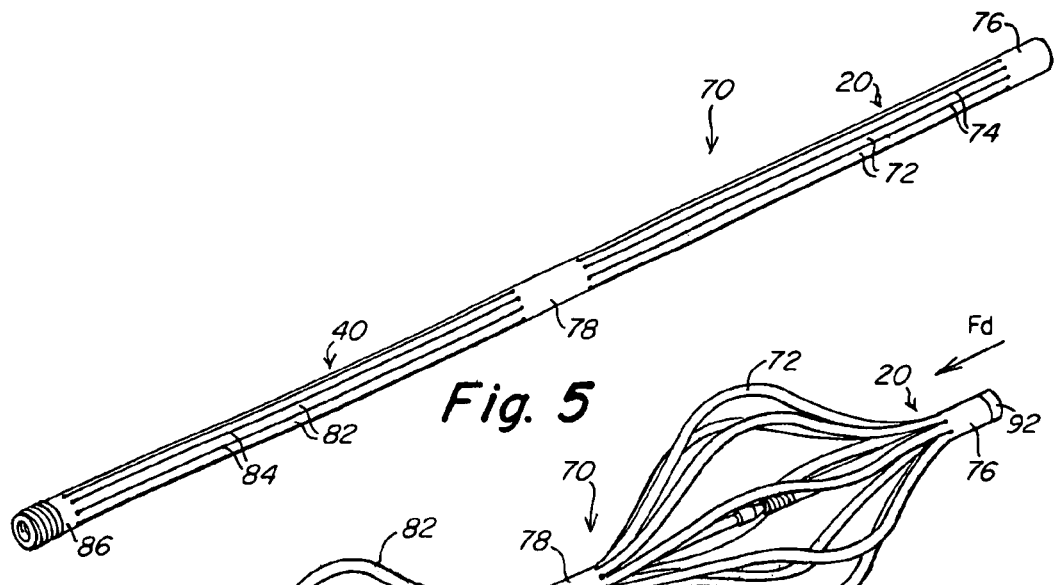
FIGS. 5-8 illustrate an occluder according to the present invention in a sequence between a reduced profile delivery configuration (FIG. 5) and an expanded profile deployed configuration (FIG. 8)
Figure 6:
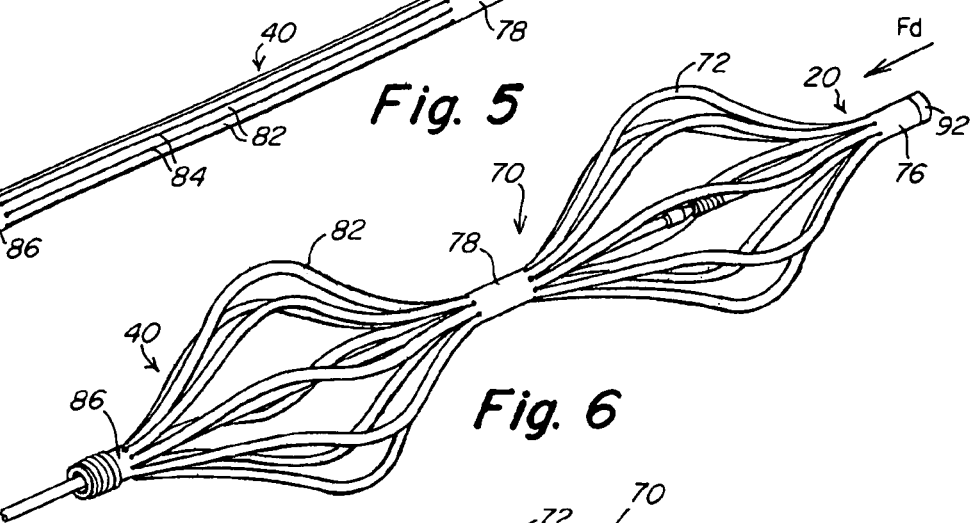
Figure 7:
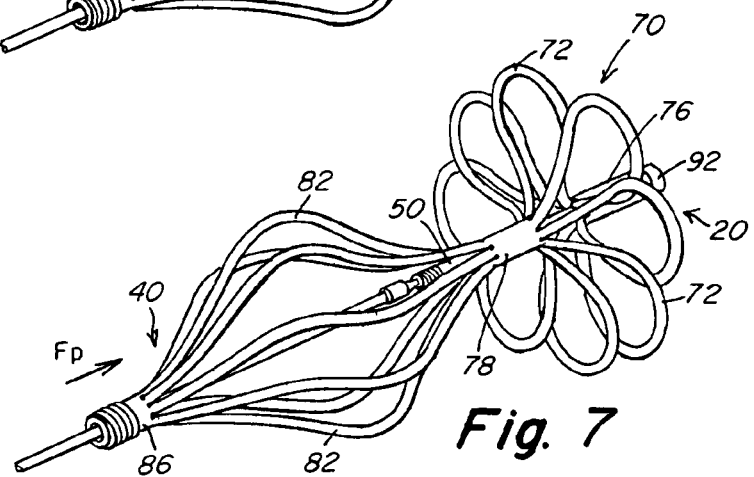
Figure 8:
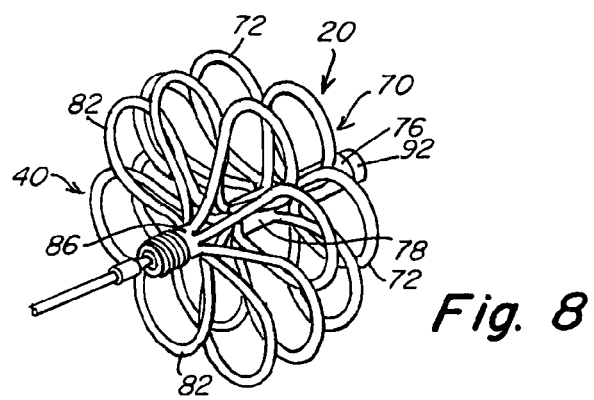

As shown in FIGS. 5-8, the occluder 70 is formed from a tube (which can be extruded or rolled), or alternately from a plurality of filaments that have been bonded together, that forms distal petals 72 produced by slits 74 in the distal portion of tube according to the cutting pattern shown in FIG. 5. As shown in FIG. 6, the distal portion 20 of the tube includes eight slits 74 that form eight extended segments of the tube that form the distal loops or petals 72. As apparent from the figures, the slits extend the entire distance of the distal portion of the tube between central tube 78 and distal end 76 so that the loops of the same cross-section are formed. Upon application of force $F_d$ to distal end 76, extended segments defined by slits 74 bow and twist outward to form distal petals 72 in distal side of the occluder 70. The movement of the segments during deployment is such that the segments may rotate in an orthogonal plane relative to the axis of the device. Central tube 78 may be constrained during the application of force $F_d$, or any combination of forces sufficient to reduce the axial length of the occluder may be applied. One end of each of distal petals 72 originates from central tube 78, while the other end originates from distal end 76 (FIGS. 6 and 7). Proximal petals 82 may be formed in the proximal portion 40, as shown in FIGS. 6-8, by making slits 84 between central tube 78 and proximal end 86, using the same cutting pattern described above and applying force $F_p$ or a combination of forces sufficient to reduce the axial length of the tube allowing slits 84 to bow and twist outward to form proximal petals 82 in proximal portion 40 of the occluder 70. One end of each of distal petals 82 originates from central tube 78, while the other end originates from proximal end 86.

The tube(s) or filaments forming occluder 70 may be formed from a biocompatible metal or polymer. In at least some embodiments, the occluder 70 is formed of a bioabsorbable polymer, or a shape memory polymer. Shape memory polymers can be advantageous so that the structure of the device assists in pressing the PFO tunnel closed. In other embodiments, the occluder 70 is formed of a biocompatible metal, such as a shape memory alloy (e.g., nitinol). The thermal shape memory and/or superelastic properties of shape memory polymers and alloys permit the occluder 70 to resume and maintain its intended shape in vivo despite being distorted during the delivery process. Alternatively, or additionally, the occluder 70 may be formed of a bioabsorbable metal, such as iron, magnesium, or combinations of these and similar materials. Exemplary bioabsorbable polymers include polyhydroxyalkanoate compositions, for example poly-4-hydroxybutyrate (P4HB) compositions, disclosed in U.S. Pat. No. 6,610,764, entitled Polyhydroxyalkanoate Compositions Having Controlled Degradation Rate and U.S. Pat. No. 6,548,569, entitled Medical Devices and Applications of Polyhydroxyalkanoate Polymers, both of which are incorporated by reference in their entirety.

The cross-sectional shape of the tube may be circular or polygonal, for example square, or hexagonal. The slits 74, 84 may be disposed on the face of the polygon (i.e., the flat part) or on the intersection of the faces.

The tube can be injection molded, extruded, or constructed of a sheet of material and rolled into a tube. The sheet of material could be a single ply sheet or multiple ply. The slits that form the segments could be cut or stamped into the sheet prior to rolling the sheet into a tube to connect the ends to form an enclosed cross section. Various geometrical cross sections are possible including circular, square, hexagonal and octagonal and the joint could be at the vertex or along the flat of a wall if the cross section is of a particular geometry. Various attachment techniques could be used to join the ends of the sheet to form a tube, including welding, heat adhesives, non-heat adhesives and other joining techniques suitable for in-vivo application.

The petal configuration, illustrated in FIG. 8, is the deployed configuration. The occluder 70 can be secured in the deployed configuration by a catch system that holds the ends of the tube together, certain embodiments of which are described below.

The transformable design of occluder 70 enables occluder 70 to be delivered in a reduced profile, delivery configuration and to be converted readily, i.e., by reducing the axial length, in place to the expanded profile deployed configuration. Moreover, the conversion can readily be effected by forcing distal end 76 and proximal end 86 to move toward each other. For example, distal portion 20 and proximal portion 40 of occluder 70 may be deployed in separate steps, or both distal portion 20 and proximal portion 40 of occluder 70 may be exposed (e.g., out of the delivery catheter) prior to engaging the catch system and deployed together as the catch element is engaged. Use of the terms distal and proximal portion 20 and 40, respectively, include the loops or other geometries and configurations that are formed on the distal and proximal sides, respectively.

Occluder 70 may be made in any one of several ways. Slits 74 and 84 may be cut such that tube bends into its intended configuration following deployment in vivo. Specifically, slits 74 and 84 may be cut to produce segments 72 and 82 (as illustrated in FIGS. 5, 6) of a thickness that facilitates the bending and formation of loops 72 and 82 (as illustrated in FIGS. 7, 8) upon the application of forces $F_d$ and/or $F_p$ during deployment. The segments 72, 82 that form the loops are referenced with the same reference numeral. As an alternative, or additionally, a tube formed of a shape memory material may be preformed into its intended configuration ex vivo so that it will recover its preformed shape once deployed in vivo. According to at least some embodiments, this preforming technique produces more reliable deployment and bending of occluder 70 in vivo. An intermediate approach may also be used: tube may be only slightly preformed ex vivo such that it is predisposed to bend into its intended shape in vivo upon application of forces $F_d$ and/or $F_p$. An occluder formed from filaments can similarly be preformed ex vivo.

FIG. 2 shows a deployed occluder 70 in a human heart with a catch member 50 engaged (much of the catch member is obscured by the central tube of the occluder). The term "catch system" describes the components or portions/aspects of a device that is secures the occluder in the deployed configuration; it may be a single piece or a group of connected or assembled pieces. In embodiments described herein, a catch system includes a catch member substantially disposed within an axial passage of the occluder that engages with the ends of the occluder to hold the occluder in the deployed configuration. The axial passage can be radially central in some embodiments. The catch member is described in more detail below. This particular type of occluder 70 and delivery sequences are described for purposes of illustration and explanation; of course, other types of occluders can be deployed using the catch systems described herein.

The catch member 50, as illustrated, is disposed in a radially central location in the occluder 70 and is schematically illustrated as a separate piece than the occluder 70. In a preferred embodiment, the distal end of the catch member includes a flange 92 (shown in FIGS. 6-8) that rests against, but not fixed to, the distal end 76 of the occluder 70. When the catch member 50 is pulled in the proximal direction, the flange 92 applies a force $F_d$ to the distal end 76 of the occluder 70 and moves it in the proximal direction. In general, references to "occluder 70" herein may be inclusive of catch member 50, depending on the context, for example, unless separately listed or otherwise stated.

One end of the occluder, preferably the proximal end 86 of the occluder 70, is able to move with respect to the catch member 50 (and especially the catch system provided thereby) so that the distal and proximal petals 72 and 82 can move from the delivery configuration to the catch deployed configuration. When the proximal end of the catch member 50 is connected with the proximal end 86 of the occluder 70, the occluder is secured in its deployed configuration.

Figure 3:
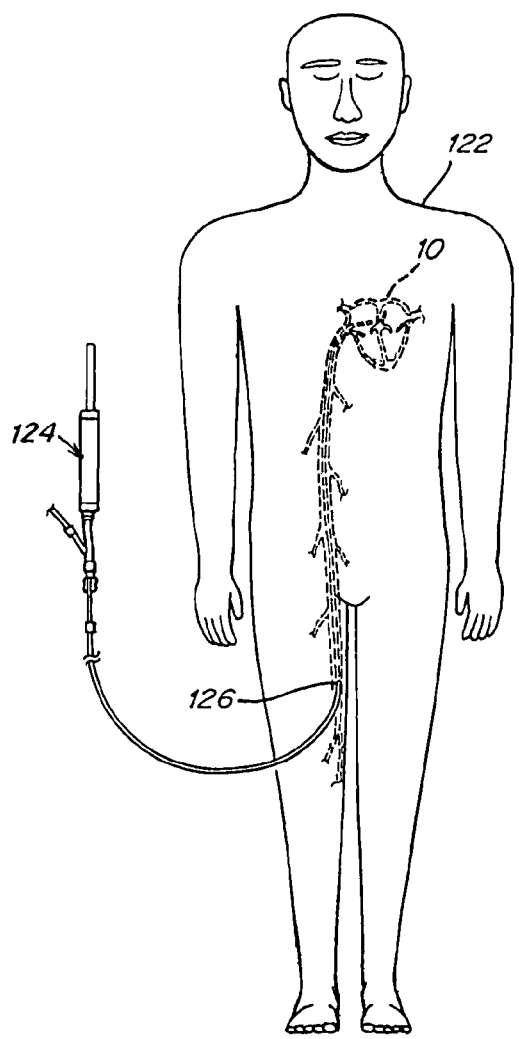
FIG. 3 illustrates introduction of the occluder in a human heart using a delivery system in accordance with an aspect of the invention.
Figure 4:
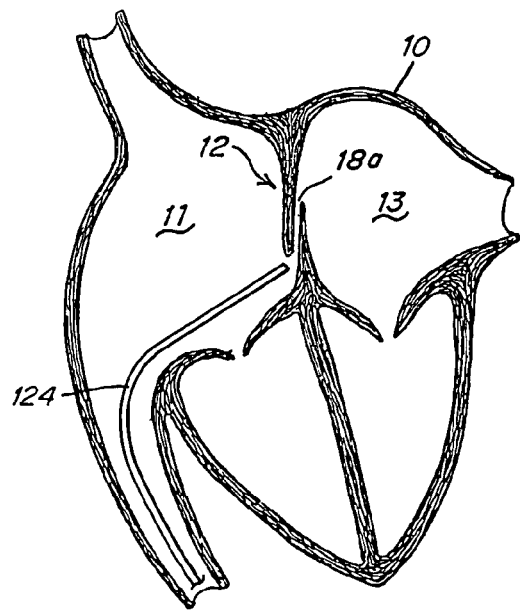
FIG. 4 illustrates a detail view of a delivery catheter in a heart with its tip approaching a patent foramen ovale between the left atrium and right atrium.

FIG. 3 illustrates the insertion of an occluder in a human subject 122 using a delivery assembly 124 in accordance with an aspect of the disclosure. A portion of delivery assembly 124, including an occluder and a delivery mechanism for the occluder, which can be externally manipulated by a clinician, is inserted into the subject through an incision point 126. The distal end of the delivery assembly is advanced toward and into the heart 10 until the distal end is in proximity to the defect to be closed, as seen in FIG. 4.

One embodiment of a delivery system 250 of the present invention will now be described with reference to FIGS. 9-12. As used herein, when connected to an occluder and/or catch member, the term "delivery system" may include those components. FIG. 9 is an exploded perspective view of the components of the delivery system 250 including a catch member 50 that can be disposed in the radially central portion of the occluder 70. The illustrated system 250 further includes a delivery catheter 172 with its distal end 178 for holding the proximal end 86 of the occluder 70 during its delivery, deployment, and retrieval, an inner catheter 168 slidably disposed within the delivery catheter 172 with a key 166 at its distal end, and a delivery wire 164 slidably disposed within the inner catheter 168 designated to connect with the catch member 50 with a threaded portion 162 at its distal end. The catch member 50 includes flange 92 at the distal end. The flange 92 rests against the distal end 76 of the occluder 70, so that when a force $F_d$ is applied to catch member 50, the distal end of the occluder 70 moves along with catch member 50 in the proximal direction. The distal end of the catch member 50 is allowed to freely rotate relative to the occluder 70, for reasons that are made clear as the operation of the device is described below. Typically the catch member 50 has an axial length of about 5-30 mm and a diameter of approximately 0.5-3 mm. The axial length of the catch member 50 is related to the axial length of the occluder in the deployed configuration. Although the catch member 50 is illustrated as a circular cylinder, a variety of cross sectional shapes can be used effectively.

According to one embodiment, catch member 50 is made of any metal or polymer. In another embodiment, catch member 50 is made of biocompatible metal or polymer. In an alternative embodiment, catch member 50 is made of bioabsorbable or shape memory material.

In a specific embodiment, catch member 50 is made of shape memory material (e.g., nitinol). The thermal shape memory and/or superelastic properties of shape memory polymers and alloys permit the catch member 50 to resume and maintain its intended shape in vivo despite being distorted during the delivery and/or deployment process.

In one embodiment, catch member 50 is made of a bioabsorbable material. Exemplary bioabsorbable materials include polymers, such as polyhydroxyalkanoate compositions, for example poly-4-hydroxybutyrate (P4HB) compositions, disclosed in U.S. Pat. No. 6,610,764, entitled Polyhydroxyalkanoate Compositions Having Controlled Degradation Rate and U.S. Pat. No. 6,548,569, entitled Medical Devices and Applications of Polyhydroxyalkanoate Polymers, both of which are incorporated by reference in their entirety.

The proximal end 160 of the catch member 50 includes external threads 152 that cooperate with internal threads 154 of the proximal end 86 of the occluder 70. When engaged, the threaded connection formed by threads 152 and 154 operates to hold the occluder 70 in the deployed configuration. The connection can be released by unthreading the catch member 50 from the proximal end of the occluder 70. Once the connection is released, the occluder 70 can collapse into its delivery configuration and be retrieved.

In the illustrated embodiment, The proximal end 160 of the catch member 50 also includes internal threads 158 and a slot 156 (shown in dashed lines) disposed at the radial center of the catch member 50. In other embodiments, the internal threads 158 can be disposed anywhere along the length of catch member 50, i.e., at the proximal or distal ends or more centrally. The internal threads 158 are designed to cooperate with external threads 162 of the distal end of the delivery wire 164. When engaged, the threaded connection formed by threads 158 and 162 allows a force Fd to be applied to the catch member 50 when the delivery wire 164 is pulled in the proximal direction. To release the delivery wire after the deployment of the occluder 70, the threaded connection between threads 158 and 162 is disengaged.

In addition to the threaded portion 154 at the proximal end 86 of the occluder 70 to secure the catch member 50, the occluder can include additional internal threads at the center joint or connection member 78. For example, as illustrated, the connection member 78 may have threads 79 that can cooperate with the threads 152 on the catch member 50 to secure the occluder in an intermediate position. Of course, as with all the embodiments, the number of threads can vary. That is, more or fewer threads can be provided than illustrated in the exemplary embodiment.

Other mechanisms for connecting the delivery wire 164 and catheter 168 are also possible. Although FIG. 9 shows the delivery wire 164 designed to connect with the catch member 50 by a threaded connection, the connection between the delivery wire 164 and the catch member 50 can be any other suitable mechanism as described in, for example, U.S. patent application Ser. No. 11/235,661, incorporated by reference herein in its entirety. In specific embodiments, the delivery wire 164 can also be connected with the catch member 50 by any other suitable means, including various types of wire or other long flexible material. For ease of reference, the delivery wire is intended to include all long, flexible materials that are suitable for the intended purpose described. In some embodiments, it may be advantageous to have the delivery wire be able to translate an axial pushing force. If a sufficiently thin material is used, the delivery wire 164 can be cut to release the delivery wire 164 after the deployment of the occluder 70. Other embodiments are described below.

The delivery wire 164 is disposed inside inner catheter 168 and can freely slide or rotate relative to the inner catheter 168. The inner catheter 168 is slidably disposed within the delivery catheter 172. The inner catheter 168 can also extend inside the radially central portion of occluder 70 and can freely rotate or slide relative to the occluder 70. Disposed at the distal end 170 of the inner catheter 168 is a key 166 that can be inserted into the slot 156 at the proximal end 160 of the catch member 50. When inserted, the key 166 of the inner catheter 168 fits the slot 156 at the proximal end 160 of the catch member 50, so that by rotating the inner catheter 168, the catch member 50 can be rotated. Hence, upon inserting the key 166 of the inner catheter 168 to the slot 156 at the proximal end 160 of the catch member 50, the inner catheter 168 can be used to threadably engage or disengage the external threads 152 at the proximal end 160 of the catch member 50 with internal threads 154 of the occluder 70.

FIGS. 10 and 11 are end views of the catch member and inner catheter of the delivery system 250 illustrated in FIG. 9, as seen along lines 10-10 and 11-11 respectively. Although the cross-section of the key 166 of the inner catheter 168 and the slot 156 at the proximal end 160 of the catch member 50 are shown as squares, a variety of cross-sectional shapes can by used effectively.

The delivery system includes a delivery catheter 172 for holding the proximal end 86 of the occluder 70 during the deployment or retrieval of the occluder 70. The distal end 178 of the delivery catheter 172 includes internal threads 174 that cooperate with external threads 176 at the proximal end 86 of the occluder. The delivery catheter 172 can be threadably connected to the occluder 70 using threads 174 and 176. When applying a force $F_d$ to the distal end 76 of the occluder 70, the delivery catheter 172 can hold the position of the proximal end 86 of the occluder 70, or apply a force $F_p$ in the opposite direction of force $F_d$, so that the axial length of the occluder 70 is reduced and the occluder 70 is transformed from the delivery configuration into the deployed configuration. Once the occluder 70 is deployed, the delivery catheter 172 can be disconnected from the occluder 70 and removed.

Although FIG. 9 shows the delivery catheter 172 designed to connect with the occluder 70 by a threaded connection, the connection between the delivery catheter 172 and the occluder can be any other suitable mechanism as described in, for example, U.S. patent application Ser. No. 11/235,661, incorporated by reference herein in its entirety.

Figure 12:
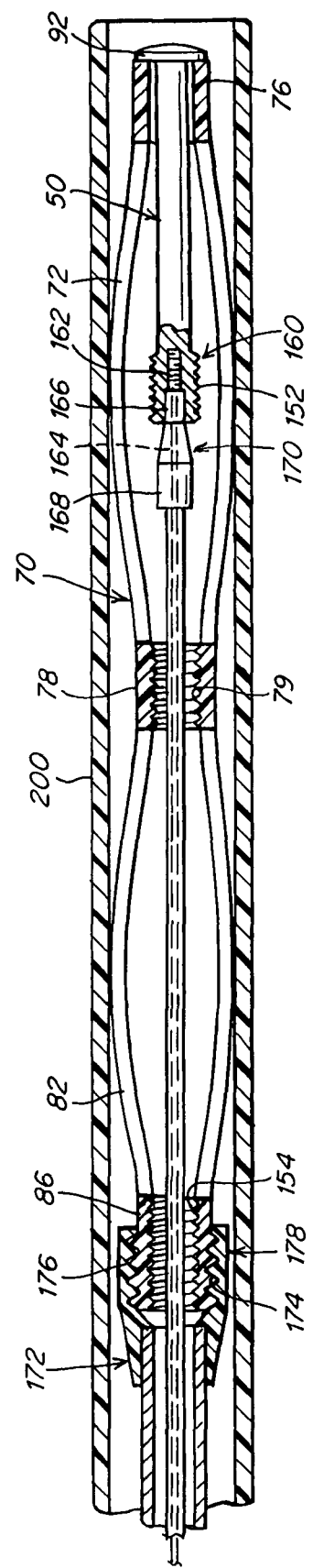
FIG. 12 is a axial cross-sectional detail view of a delivery system with an occluder in accordance with an embodiment of the present invention within a delivery catheter.

FIG. 12 is a cross-sectional detail view of the delivery system, catch member 50 and the occluder 70 illustrated in FIGS. 9-11 within a delivery sheath 200. As shown, the delivery catheter 172 is connected with the proximal end 86 of the occluder 70. The inner catheter 168 is in contact with the proximal end 160 of the catch member 50, with the key 166 at the distal end inserted into the slot 156 at the proximal end 160 of the catch member 50. The delivery wire 164 is disposed inside the inner catheter 168 and is shown in phantom lines. The delivery wire 164 is attached to the proximal end 160 of the catch member 50. The flange 92 at the distal end of the catch member 50 is in contact with the distal end 76 of the occluder 70. The occluder 70 is in a reduced profile, delivery configuration so that it fits within the delivery sheath 200. Using the delivery sheath 200, the occluder 70 and the catch member 50 can be inserted into or retrieved from a human subject as illustrated in FIG. 3.

As illustrated in FIG. 12, various components of the delivery system, the catch member 50 and the occluder 70 can be connected and placed inside the delivery sheath 200 before deployment. After moving the distal end of the delivery sheath 200 past an aperture in the septum, the delivery sheath 200 can be removed, exposing the occluder 70. The delivery wire 164 and the delivery catheter 172 can then be used to convert the occluder 70 from the delivery configuration to the expanded profile, deployed configuration to occlude the aperture. The inner catheter 168 and delivery wire 164 can then be used to connect and engage the proximal ends 160 of the catch member 50 and proximal ends 86 of the occluder 70 so that the occluder 70 maintains the deployed configuration. Then, the delivery catheter 172 and inner catheter 168 can be detached from the occluder 70 and removed. With the delivery wire 164 still connected to the catch member 50, the deployment of the occluder 70 can now be assessed. If deployment of the occluder 70 is not satisfactory, the occluder 70 can be retrieved. Upon satisfaction with the deployment of the occluder 70, the delivery wire 164 can be removed. In an alternate sequence, the delivery wire 164 and inner catheter 168 can be detached from occluder 70 first. The position can be assessed with the delivery catheter 172 in place. The delivery catheter 172 can then be removed.

If retrieval is needed, the inner catheter 168 can be disposed inside the delivery catheter 172, which can be disposed inside the delivery sheath 200 and advanced together into the heart. In addition, the delivery wire 164 can be disposed inside the inner catheter 168 and inserted together with the inner catheter 168. The delivery catheter 172 engages the proximal end 86 of the occluder 70, and the delivery wire 164 engages the proximal end 160 of the catch member 50. The inner catheter 168 and delivery wire 164 is used to rotate the catch member 50 to disengage its proximal end 160 from the proximal end 86 of the occluder 70. After the occluder 70 returns to its reduced profile, delivery configuration, the occluder 70 and the catch member 50 can be withdrawn together with the delivery sheath 200.

FIGS. 13 and 14 are partial cross-sectional views of a delivery assembly 124 in accordance with an aspect of the disclosure. Delivery assembly 124 includes an occluder 70 and a catch member 50 at the distal end. As shown in FIG. 13, delivery assembly 124 has four coaxial components, which make up the delivery system 250, disposed next to the occluder 70, which are the delivery wire 164, the inner catheter 168, the delivery catheter 172, and the delivery sheath 200. As FIG. 14 illustrates, the delivery wire 164, the inner catheter 168, the delivery catheter 172, and the delivery sheath 200 can all freely slide and rotate with respect to each other. The motion of these components can be controlled by an apparatus 202 disposed at the proximal end of the delivery assembly 124. Apparatus 202 can be manipulated externally from the body by a clinician.

FIG. 14 illustrates the types of movement possible at the proximal end of the delivery system that can deploy the occluder 70 with a catch member 50 according to an embodiment of the present invention. As illustrated in FIG. 14, one embodiment of the invention can be delivered by the use of a delivery system that can be manipulated in several axial (back and forth) and rotational (around an axis) directions. Particularly, the delivery sheath 200 can be moved axially by movement D and (optionally) rotationally by the movement H. Directional arrows at the proximal side illustrate the direction of movement an operator would effect to move in the same direction at the distal side. The proximal portion is on the upper part of FIG. 14 and the distal side is on the lower portion of FIG. 14. The delivery catheter 172 can be moved axially by movement A and rotationally by movement E. The inner catheter 168 can be moved in the axial direction by movement B and rotationally by movement G. Finally, the delivery wire 164 can be moved axially by movement C and rotationally by movement F. Of course, various combinations of movements are possible and desirable, for example during delivery of the occluder 70 to the desired delivery site through the blood vessels, all the components will be moved together.

FIG. 15 is an expanded view of a delivery system 300 in accordance with another embodiment of the present invention. Similar to the delivery system 250 illustrated in FIGS. 9-12, this delivery system 300 includes a catch member 256 that can be disposed in the radially central portion of the occluder 70, a delivery catheter 252 with its distal end 178 for holding the proximal end 86 of the occluder 70 during its delivery, deployment, and retrieval, a inner catheter 258 slidably disposed within the delivery catheter 252 with a slot 274 at its distal end, and a delivery wire 260 slidably disposed within the inner catheter 258 designed to connect with the catch member 256. The proximal end 254 of the catch member 256 includes external threads 264 that cooperate with internal threads 266 of the proximal end 86 of the occluder 70. When engaged, the threaded connection 264 and 266 operate to hold the occluder 70 in the deployed configuration. When the proximal end 254 of the catch member 256 and the proximal end 86 of the occluder 70 are disengaged, the occluder 70 can collapse into its reduced profile, delivery configuration and be retrieved. The catch member 256 includes a flange 262 at the distal end that rests against the distal end 76 of the occluder 70.

Figure 18A:
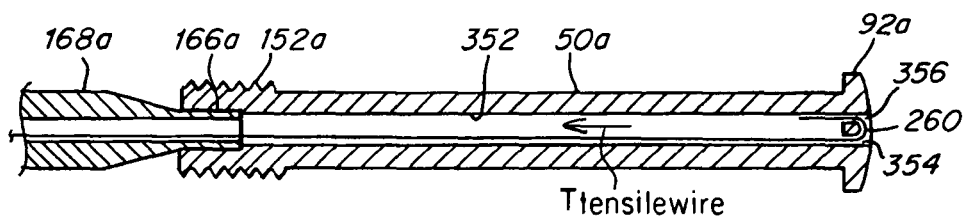
FIGS. 18A-18C are cross-sectional schematic drawings of another embodiment of the invention with a wire connection between the catch member and the delivery wire.

Different from the delivery system 250 shown in FIG. 9, the delivery wire 260 engages the catch member 256 by forming a loop around the distal end of the catch member 256. As illustrated, two apertures may be formed within the catch member 256 to secure the delivery wire 260. As illustrated in FIG. 18A, in this embodiment, the catch member 256 includes an axial passageway 268 sufficient to allow the wire to be disposed within. The distal end of the catch member 256 has two apertures 270 which communicate with the axial passageway. The delivery wire 260 extends distally through the first aperture, bends, and returns through the second aperture. During occluder delivery, the distal end of the delivery wire 260 extends to a general proximal direction. By pulling the delivery wire 260 in the proximal direction, a force Fd can be applied to the catch member 256 and the distal end 76 of the occluder 70. After the deployment of the occluder 70, the delivery wire 260 can be removed.

An inner catheter 258 is disposed inside the central portion of the occluder 70 and can freely rotate or slide relative to the occluder 70. The distal end of the inner catheter 258 includes a slot 274 that fits a key 272 disposed at the proximal end of the catch member 256. Using the inner catheter 258, the catch member 256 can therefore be rotated to engage the proximal end 86 of the occluder 70 locking the occluder in the deployed configuration. This delivery system 300 can be used to deploy occluder 70 in generally the same manner as the delivery system described in connection with FIGS. 9-12.

FIGS. 16 and 17 are end views of the catch member and inner catheter of the delivery system 300 as seen along lines 16-16 and 17-17, of FIG. 15 respectively. The cross-sectional shape of the key 272 at the proximal end of the catch member 256 and the slot 274 of the inner catheter 258 are not limited to what is illustrated in FIGS. 15-17; various other cross-sectional shapes can be used effectively.

Figure 18B:
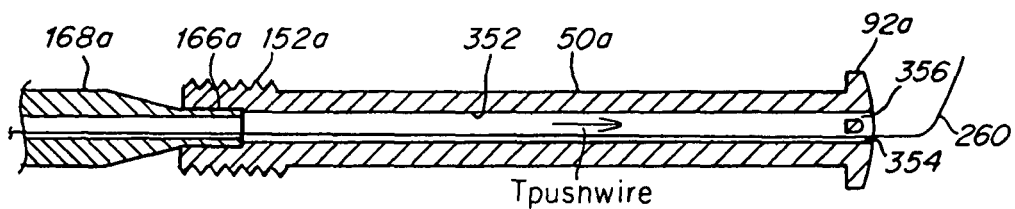
Figure 18C:
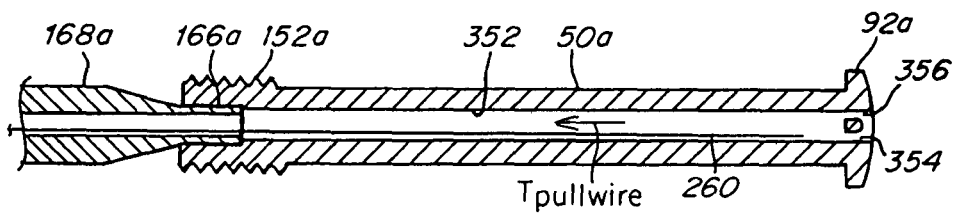

FIGS. 18A-18C illustrate the function of the delivery wire 260 during occluder delivery and its removal after occluder deployment. As illustrated in detail cross-sectional view, with similar reference numerals being given an "a". For example, the catch member is "50a". In this embodiment a delivery wire 260 is provided that can transmit a pushing force along its axial length so that a pushing force applied at the proximal end of the delivery wire 260 can push the delivery wire 260 distally. The delivery wire 260 is disposed in an axial passageway 352 in the catch member 50a. The delivery wire 260 extends distally through the first aperture 354, bends, and returns through the second aperture 356. During occluder deployment, catch member 50a extends proximally by a pulling force $T_{tensilewire}$, and the delivery wire 260 remains in place in the aperture as illustrated in FIG. 18A. To remove delivery wire 260, as illustrated in FIG. 18B, a force $T_{pushwire}$ is applied, the delivery wire 260 extends distally. Distal end of the delivery wire 260 is then freed from the second aperture, and therefore the delivery wire 260 is disconnected with the catch member 50a. Then, a force $T_{pushwire}$ is applied, the delivery wire 260 is removed as illustrated in FIG. 18C. In some embodiments, the delivery wire material could be 304SS stainless steel flat wire or nitinol.

Figure 19:
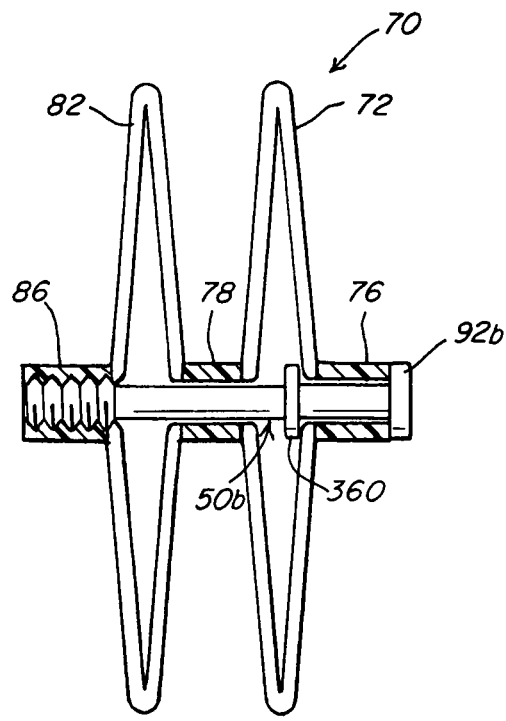
FIG. 19 illustrates a schematic view of a catch member according to another embodiment of the invention; and, FIG. 20 illustrates a schematic view of another embodiment of the invention.

FIG. 19 illustrates another embodiment of a catch member 50b that can be used with various embodiments of the invention described herein. In this embodiment, the occluder 70 is designated with numbers consistent with previous embodiments. A catch member 50b includes a flange or ridge 360 at the proximal side of the distal end 76 in addition to a distal flange 92b. According to this embodiment, the flanges 360 and 92b are able to restrain the axial movement of the distal end 76 of the occluder with respect to catch member 50b. The catch member 50b may be allowed to rotate with respect to the occluder or not depending on the configuration of other parts of the catch system. In a preferred embodiment, the ridge 360 is disposed adjacent to the distal end of the catch member 50b. The distance between the ridge 360 and the distal flange 92b is approximately equal to the axial length of the tubular distal end 76 of the occluder 70. The ridge 360 has a radial size approximately equal to the distal flange 92b, but the size could be smaller or larger in various embodiments. The center ridge 360 facilitates pushing of the distal end 76 if retrieval of the occluder 70 is desired. The center ridge 360 thus can be used to collapse the occluder 70.

Figure 20:
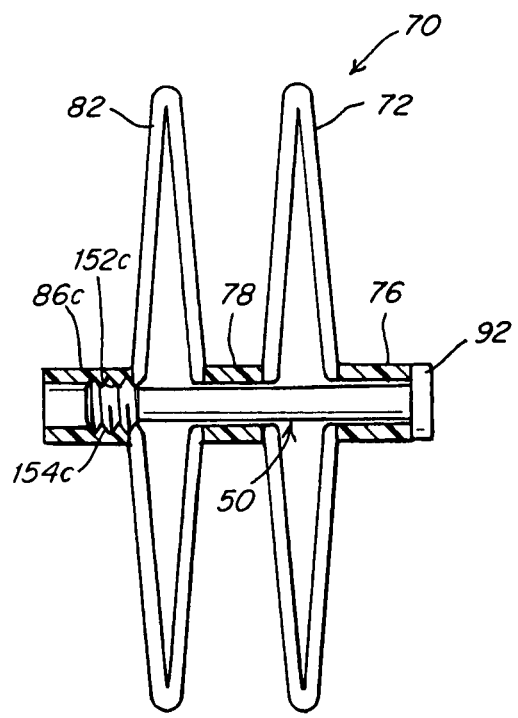

It will be understood that the threads 152 and 154, 174 and 176 can be of constant or varying pitches. In various embodiments, the threads could be v-form, square or acme threads, for example. FIG. 20 illustrates an embodiment of the invention such that the threaded portions 152c and 154c that are used to secure the catch member 50 to the tube does not extend the entire axial distance of the proximal end 86c. In another embodiment, the threaded portion does extend the entire axial distance of the proximal end 86c. In another embodiment, the threaded portion extends the entire length of the catch member 50.

The embodiments and techniques described here are described preferably for use with a device made of a polymer and formed from a single tube. While the device is thus shown as being substantially formed from a single tubular body, which could also be made of cylindrically arranged filaments, the catch mechanism as described in the embodiments above could be used with other types of devices, including those formed from many pieces, and including devices formed from other materials, including metals, polymers, stainless steel or nitinol.

The term "bioabsorbable," as used in the description above, is also understood to mean "bioresorbable."

While the description above refers to "wires", and while the term "wire" might convey a more rigid piece than a string, a suture or a filament, all these terms are essentially interchangeable with respect to the invention and any suitable element can be used. Each wire, string, suture and filament can be composed of one or more wires, strings, sutures and filaments.

In cases in which the device is made of a polymer, it can be desirable to add an additive or coating to the material to make it radiopaque to make it more visible in a wider variety of imaging techniques.

It will be appreciated that while a particular sequence of steps has been shown and described for purposes of explanation, the sequence may be varied in certain respects, or the steps may be combined, while still obtaining the desired deployment or in some cases to effect deployment in a particular way. For example, the delivery sheath may be advanced or retracted at varying times and in varying degrees, the proximal and distal portions of the occluder may be deployed into the petal configuration in a different sequence, etc. In addition, the steps could be automated.

It will be appreciated that the particular embodiments illustrated and described herein are provided by way of example only and are not intended to limit the scope of the invention, which is indicated in the appended claims.

What is claimed is:

1. A collapsible medical device for occluding an aperture in a body, the medical device having a first configuration with a reduced profile and a second configuration with an expanded profile, the medical device being adapted to be delivered through a delivery system into a desired delivery location, the medical device comprising:
   a proximal end, a distal end, a center joint, an axial passage along the length of the medical device;
   a catch member having a proximal end, a distal end, and an axial passageway, the catch member adapted to be disposed in the axial passage of the medical device such that the medical device can move from the first configuration to the second configuration with the catch member in the passage; and
   a delivery wire disposed within the axial passageway, the delivery wire operable to transmit a pushing force and a pulling force;
   wherein each of the proximal end of the medical device and the proximal end of the catch member comprises threads;
   wherein the proximal end of the catch member is capable of rotating relative to the proximal end of the medical device, thereby forming a threaded connection with the proximal end of the medical device;
   wherein the distal end of the catch member includes two apertures on the distal end for attaching the delivery wire and is operable to engage a distally disposed hook member of the delivery wire such that applying the pulling force to the delivery wire pulls the catch member proximally, and applying the pushing force to the delivery wire disconnects the delivery wire from the catch member; and
   wherein the pushing force and the pulling force are applied to a proximal end of the wire to pull the catch member proximally or disconnect the delivery wire from the catch member.

2. The medical device of claim 1, wherein the catch member is made of bioabsorbable material.

3. The medical device of claim 1, wherein the distal end of the catch member comprises a flange that rests on the distal end of the medical device.

4. The medical device of claim 1, wherein the proximal end of the medical device includes internal threads and the proximal end of the catch member includes external threads.

5. The medical device of claim 1, wherein the two apertures comprise a first aperture and a second aperture, and the delivery wire extends distally through the first aperture, bends, and returns through the second aperture.

6. The medical device of claim 5, wherein the delivery wire extends proximally only partially along the axial passageway when the device is in the first configuration.

* * * * *